United States Patent
Hsieh et al.

[11] Patent Number: 5,864,598
[45] Date of Patent: Jan. 26, 1999

[54] METHODS AND APPARATUS FOR SCANNING AN OBJECT IN A COMPUTED TOMOGRAPHY SYSTEM

[75] Inventors: Jiang Hsieh, Waukesha; Stanley H. Fox, Brookfield, both of Wis.

[73] Assignee: General Electric Company, Milwaukee, Wis.

[21] Appl. No.: 837,545

[22] Filed: Apr. 21, 1997

[51] Int. Cl.⁶ .................................................. A61B 6/03
[52] U.S. Cl. .................... 378/4; 378/15; 378/901
[58] Field of Search ................... 378/4, 15, 19, 378/901

[56] References Cited

U.S. PATENT DOCUMENTS 5,361,291  11/1994  Toth et al. ................................ 378/12
5,546,439  8/1996  Hsieh ........................................ 378/15

Primary Examiner—David P. Porta
Assistant Examiner—David Vernon Bruce
Attorney, Agent, or Firm—John S. Beulick; Christian G. Cabou; Phyllis Y. Price

[57] ABSTRACT

The present invention, in one form, is a system for generating a high resolution image of an object from projection data acquired during a computed tomography scan. The system includes a gantry having an x-ray source which rotates around the object. The x-ray source emits an x-ray beam which is collimated with a collimator having a collimator aperture to define an x-ray beam width, or slice thickness. The projection data is reconstructed to generate image data for adjacent image slices. A deconvolution algorithm is applied to the image data to generate a deconvolved image having a finer, i.e., smaller, resolution than the collimator aperture.

20 Claims, 3 Drawing Sheets

FIG.5a(ii)

METHODS AND APPARATUS FOR SCANNING AN OBJECT IN A COMPUTED TOMOGRAPHY SYSTEM

FIELD OF THE INVENTION

This invention relates generally to computed tomography (CT) imaging and more particularly to scanning an object of interest with a CT scanner.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The detectors are generally rectangular. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. Typically, the configuration of a slice may be varied. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better use of injected contrast, improved image reconstruction at arbitrary locations, and better three-dimensional images.

In known CT systems, the x-ray beam from the x-ray source is projected through a pre-patient collimating device, or collimator, that defines the x-ray beam profile in the patient axis, or z-axis. The collimator typically includes x-ray absorbing material with an aperture therein for restricting the x-ray beam. Known apertures are typically linear, or rectangular, and the aperture width controls the slice thickness as measured along the z-axis. For example, by passing an x-ray beam through a collimator with a 1 mm aperture, the beam output from the collimator will have a 1 mm thickness.

Known CT systems typically provide adequate image resolution. However, such resolution is limited, for example, by the collimator size, the slice thickness and the filter kernel. With respect to 3D and multi-planar reformat (MRP) images, it would be desirable to improve image resolution for all collimator sizes.

Image resolution is related to slice thickness. Particularly, by reducing the slice thickness, the image resolution is improved. In some applications, a slice thickness as thin as 0.5 mm is desired. Known CT systems, however, typically are configured to provide the smallest slice thickness of 1 mm. Until now, it was believed that in order to reduce the slice thickness to 0.5 mm, significant hardware and software changes were necessary.

Image resolution also is related to the reconstruction filter kernel. Particularly, increasing the cut-off frequency of the filter kernel causes an improvement in image resolution in the x-y plane. However, increasing the filter kernel cut-off frequency also increases the high frequency contents contributing to an image, and causes significant aliasing artifacts. Accordingly, the reconstruction filter kernel in a known CT system typically must be limited. Until now, it was believed that in order to further increase the reconstruction filter kernel cut-off frequency, significant hardware and software changes were necessary.

It would be desirable to improve image resolution in a CT system by providing a slice thickness as thin as 0.5 mm. It also would be desirable to improve image resolution by facilitating the use of even higher reconstruction filter cut-off frequencies. It also would be desirable to provide such image resolution without degrading overall image quality, and without requiring significant hardware and software changes in known CT system.

SUMMARY OF THE INVENTION

These and other objects may be attained in a CT system which, in one embodiment, implements a deconvolution algorithm to provide an image resolution of less than 1 mm. Particularly, and in accordance with one embodiment of the present invention, projection data for at least two adjacent image slices is obtained. The system is configured so that the fan beam has a 1 mm slice thickness and image slices are located approximately 0.5 mm apart. The projection data of the image slices is then processed to generate image data for each image slice. The deconvolution algorithm is then applied to the image data in the z-direction to generate an image having approximately 0.5 mm z-resolution.

Using the deconvolution algorithm as described above enables generation of images having resolution of 0.5 mm with a 1 mm collimator aperture. Therefore, the 0.5 mm resolution can be achieved without having to modify the hardware in existing systems. Existing systems only need to be modified to incorporate the deconvolution algorithm. Further, the computational costs and expenses of generating such high resolution images in CT image reconstruction are not significantly increased.

BRIEF DESCRIPTION OF THE DRAWINGS

FIG. 5a(ii) is a graphic illustration of projection data acquired during the completion of a first revolution of a helical scan.

DETAILED DESCRIPTION

Figure 1:
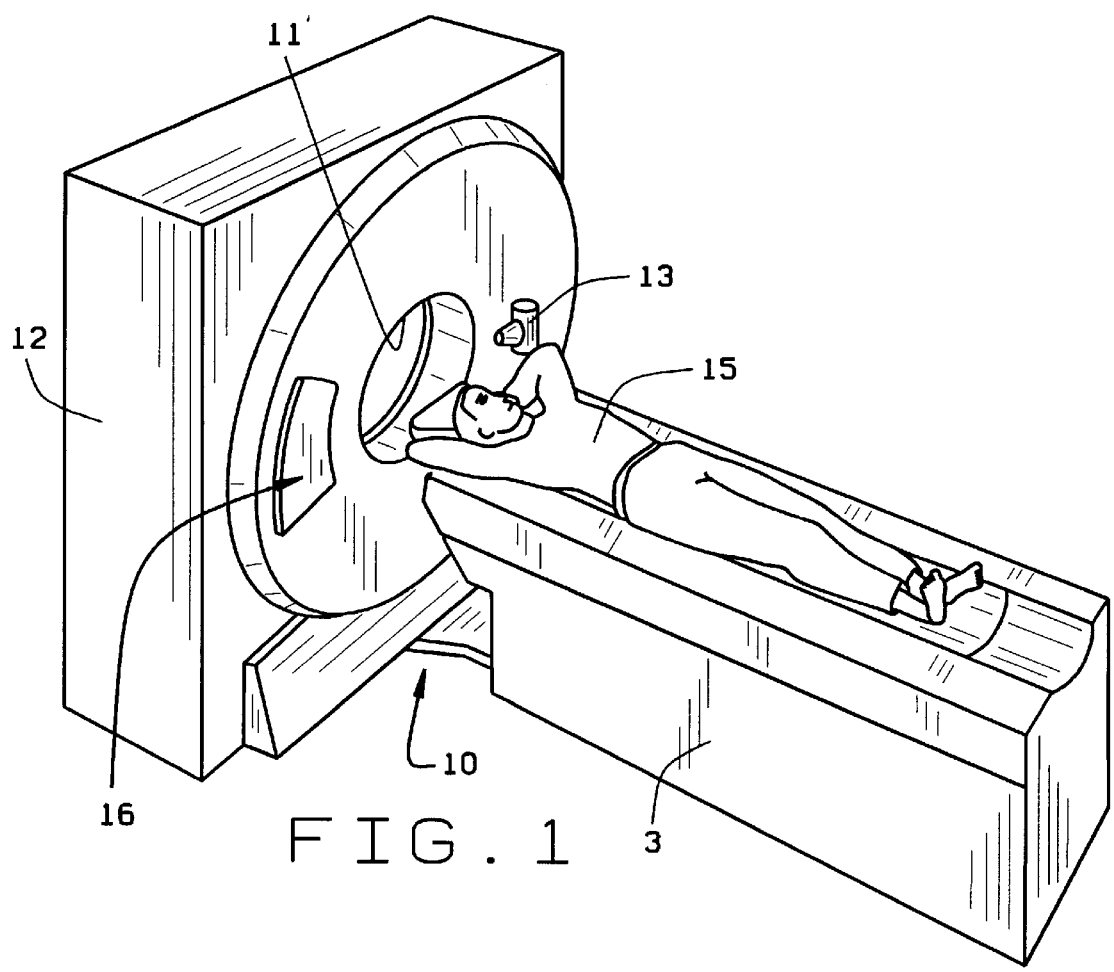
FIG. 1 is a pictorial view of a CT imaging system.
Figure 2:
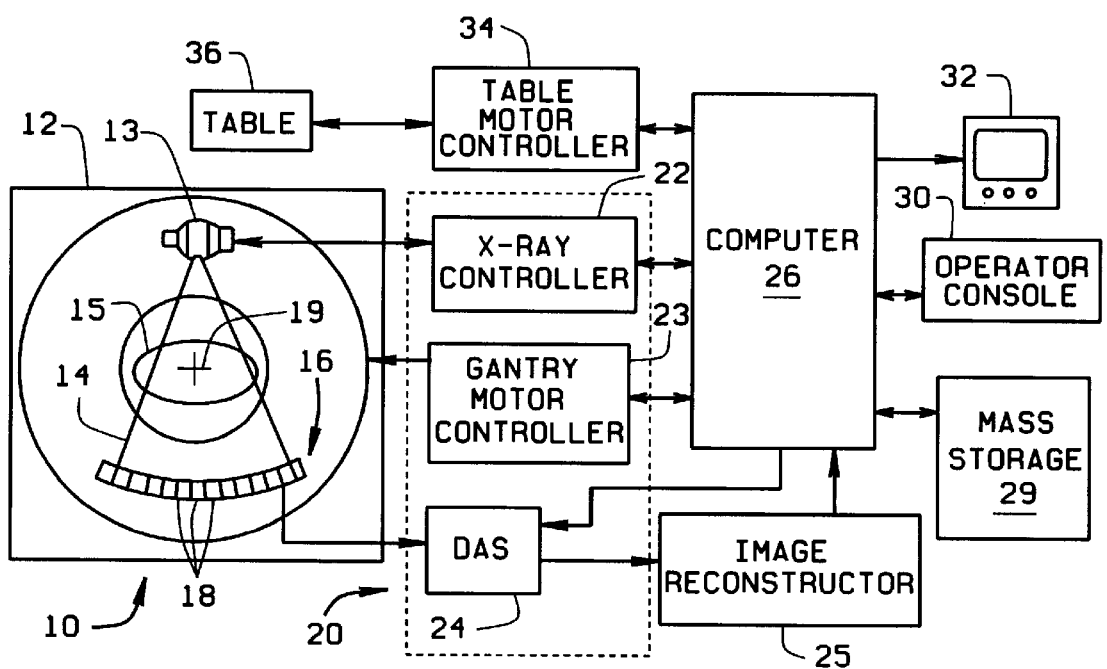
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a fan beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
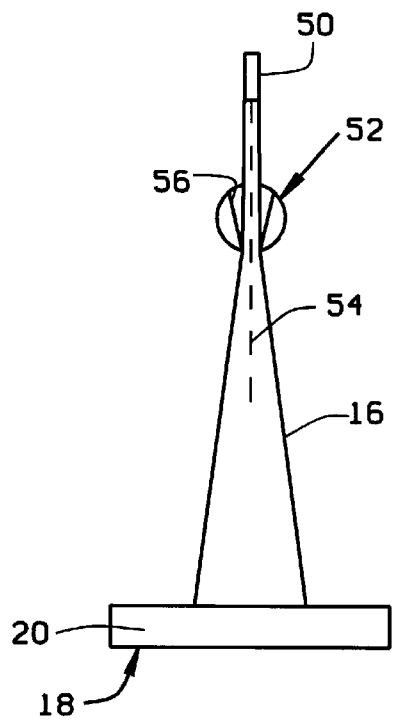
FIG. 3 is a schematic view of a CT imaging system with a collimator.

Referring to FIG. 3, and with respect to operation of x-ray source 14, x-ray beam 16 emanates from a focal spot 50 of source 14 (not shown in FIG. 3). X-ray beam 16 is collimated by a collimator 52, and collimated beam 16 is projected toward detector array 18 along a fan beam axis 54 centered within fan beam 16.

Collimator 52 has a substantially circular cross-sectional shape and an aperture 56 extends through collimator 52. A plurality of other collimator apertures (not shown) may also be formed in and extend through collimator 52, and each aperture corresponds to a particular slice width. For example, aperture 56 may correspond to a 10 mm slice width and another aperture may correspond to a 7 mm slice width. If a scan is to be performed for a 10 mm slice, then aperture 56 is aligned with expected x-ray focal spot 50 and restricts beam 16 projected from focal spot 50 to 10 mm. Collimator 52 is well known in the art. As used herein, an X mm by X mm scan refers to scanning an object of interest using an X mm collimator aperture at a 1:1 helical pitch, wherein helical pitch is the ratio of table 46 movement in one rotation of the x-ray source 14 to the slice width, or slice thickness, defined by the source collimator.

As explained above, known CT systems typically utilize collimators having at least one 1 mm aperture. While 1 mm or higher image slices are effective for many CT system applications, in some CT system applications, a thinner slice thickness is desired. Particularly, in some applications, it is desirable to generate an image with, for example, 0.5 mm slice images. Such smaller slice images are specifically desirable when patient anatomy differs in areas less than 1 mm apart. The present invention, in one embodiment, provides 0.5 mm slice images even while using a 1 mm collimator aperture.

The following discussion of a deconvolution algorithm sometimes refers specifically to CT systems using a helical or an axial scan. The deconvolution algorithm, however, is not limited to practice in connection with such systems. Further, in one embodiment, the deconvolution algorithm is implemented in "image space". However, the deconvolution algorithm may also be implemented in projection space. Also, the algorithm can be used in both single slice and multi-slice scanners. Moreover, while the algorithm is described in connection with 1 mm slice thicknesses, the algorithm may be used with other, e.g., 3 mm or 5 mm, slice thicknesses. In addition, and in one embodiment, the deconvolution algorithm would be implemented in computer 36 and would process, for example, data stored in mass storage 38. Many other alternative implementations are, of course, possible.

Figure 4A:
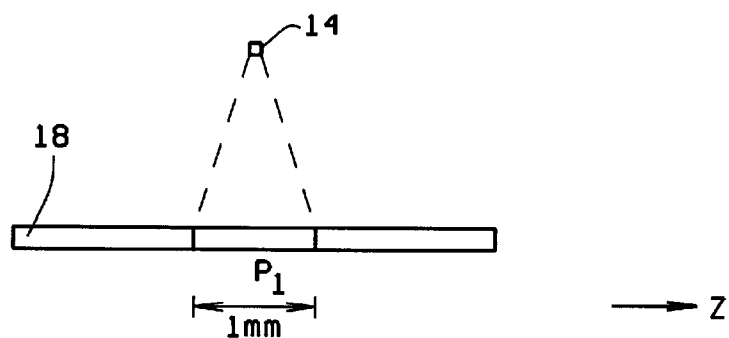
FIG. 4a is a graphic illustration of projection data acquired during a first axial scan.
Figure 4B:
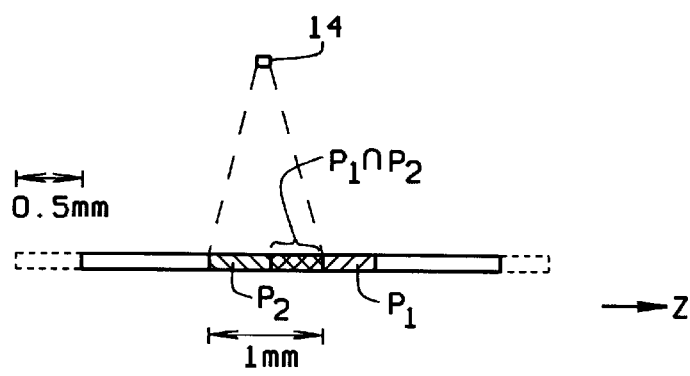
FIG. 4b is a graphic illustration of projection data acquired during a second axial scan.

In accordance with one embodiment of the present invention, x-ray source 14 is rotated at least two times during an axial scan to obtain projection data for adjacent image slices. X-ray source 14, of course, may be rotated three, four, or even more times. For example, and referring to FIG. 4a, during a first rotation of x-ray source 14, CT system 10 covers a first projection $P_1$ along a z-axis for a first image slice. As shown, the first slice includes 1 mm of projection data, and $P_1$ represents the range [0 mm, 1 mm]. After the first rotation, table 46 is advanced 0.5 mm in the z-direction. Referring to FIG. 4b, a second rotation of x-ray source 14 covers a second projection $P_2$ along the z-axis for a second image slice. As shown, the second image slice also includes 1 mm of projection data, and $P_2$ represents the range [0.5 mm, 1.5 mm]. Therefore, after two rotations of x-ray source 14, the object has moved approximately 0.5 mm, and detector array 18 has generated projection data for the range $P_1 \cup P_2$ corresponding to 1.5 mm of the object. As also shown, projection data acquired during sequential rotations at least partially overlaps in the z-axis (indicated by the range $P_1 \cap P_2$), i.e., certain projection data in each slice corresponds to an identical portion of the object. Particularly, the center 0.5 mm of the total projection data for the range $P_1 \cup P_2$ overlaps. This is sometimes referred to herein as overlapped z-axis sampling.

The projection data for the range $P_1 \cup P_2$ acquired during the two rotations of x-ray source 14, i.e., the two image slices, is filtered and backprojected in accordance with known reconstruction techniques to generate image data corresponding to each slice. Of course, if projection data for more than two image slices is obtained, then the projection data for each such slice may filtered and backprojected in accordance with known reconstruction techniques to generate image data corresponding to each slice. A deconvolution algorithm is then applied to the image data to generate high resolution images of the object. As described above, projection data generated by overlapped z-axis sampling is substantially redundant over a portion of the object. The redundant image data is deconvolved along the z-direction, i.e., in image space. Deconvolving the redundant image data generates deconvolved image data, which recovers the resolution within the overlapped sampled portion of the object.

The image data may be deconvolved, for example, with a three point kernel. Of course, the image data may be deconvolved with other kernels, e.g., two point kernels or four point kernels. When deconvolving image data with a [−0.4,1.8,−0.4] kernel, for example, and when $P_d$ denotes a resulting image, $P_o$ denotes an original image, $P_{-1}$ denotes a prior original image and $P_{+1}$ denotes a next original image, then the deconvolved image is determined in accordance with $$P_d = -0.4P_{-1} 1.8P_o - 0.4P_{+1}.$$

Other three point kernels, and other kernel sizes, of course, also may be used.

Deconvolving the image data along the z-direction facilitates improving the resolution of the deconvolved image so that such resolution is less than 1 mm. In the above example, the resolution approximates 0.5 mm, i.e., the CT system generates an image with 0.5 mm slice thicknesses.

While the above-described embodiment identifies a 1 mm collimator aperture, other size collimator apertures may be used. In addition, depending upon the desired slice thickness, table 46 may be advanced in increments either greater or smaller than 0.5 mm. In addition, the deconvolution algorithm may be applied to projection data, rather than image data. Furthermore, projection data may be generated for more than two x-ray source rotations. For example, a projection data for a third image slice may be acquired. After reconstructing such third image slice projection data, the deconvolution algorithm may be applied to the image data acquired for all three image slices. Therefore, an even smaller, i.e., better, image resolution may be obtained. Obviously, the extent of overlapping z-axis sampling is proportional to the final resolution of the deconvolved image.

The following discussion of an alternate embodiment of the present invention refers to a helical scan using a substantially 0.5:1 helical pitch. It is to be understood, however, that helical pitches other than 0.5:1 may be used. Particularly, helical pitch may be selected so that a Nyquist sampling can be substantially satisfied. For example, where a helical scan is performed with 1 mm collimation, i.e., a 1 mm collimator aperture, the slice thickness may approximate 1.2 mm because of the reconstruction algorithm. In such case, patient 22 may be scanned at a rate of 0.6 mm/sec (0.5*1.2), i.e., a 0.6:1 helical pitch, because the Nyquist criteria are satisfied. More generally, if a helical scan using a collimator having an α mm aperture generates a resulting slice thickness of β, then patient 22 may be scanned with a 0.5β:α helical pitch. Other helical pitches, e.g., helical pitches higher than 0.6:1, may, of course, be used.

Figure 5A:
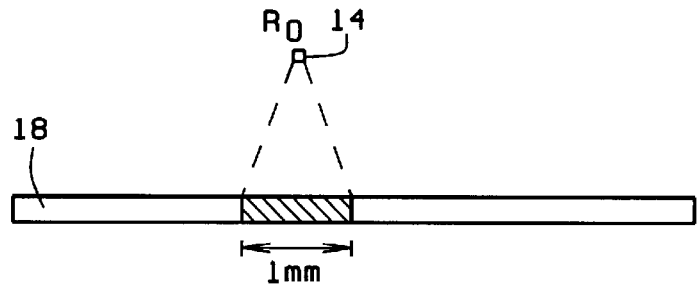
FIG. 5a(i) is a graphic illustration of projection data acquire during the beginning of a first revolution of a helical scan.
Figure 5B:
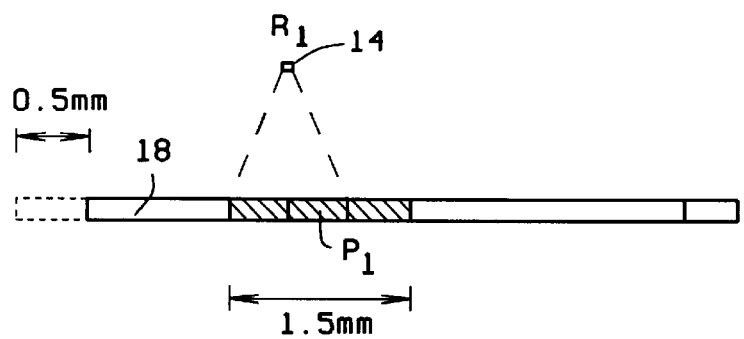
FIG. 5b is a graphic illustration of projection data acquired during a second revolution of a helical scan.
Figure 5B:
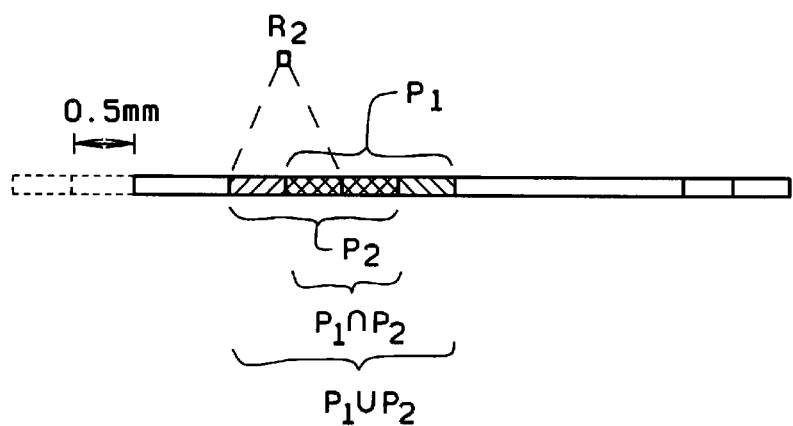

In accordance with another embodiment of the present invention, projection data is acquired with a helical scan. Particularly, during a helical scan with a substantially 0.5:1 helical pitch, and assuming x-ray source 14 includes a 1 mm collimator aperture, table 46, and thus the object to be scanned, moves 0.5 mm during each rotation of the x-ray source 14, and detector array 18 generates projection data for slice thicknesses of 1 mm in accordance with each rotation. For example, and referring to FIGS. 5a(i) and 5a(ii), during a first rotation of x-ray source 14, i.e., from $R_0$ to $R_1$, the object moves approximately 0.5 mm in the z-direction, and projection data $P_1$ is obtained covering approximately 1.5 mm of the object. Referring to FIG. 5b, and during a sequential second rotation, i.e., from $R_1$ to $R_2$, the object moves an additional 0.5 mm in the z-direction, and detector array 18 generates projection data $P_2$ covering another 1.5 mm of the object. As shown, after two rotations of x-ray source 14, i.e., from $R_0$ to $R_1$, the object has moved approximately 1 mm, and detector array 18 has generated projection data $P_1 \cup P_2$ corresponding to 2 mm of the object. As also shown, projection data acquired during sequential rotations at least partially overlaps in the z-axis (indicated by $P_1 \cap P_2$), i.e., certain projection data generated during each revolution correspond to an identical portion of the object. Particularly, the center 1 mm of the total projection data $P_1 \cup P_2$ overlaps.

Helical scanning thus provides multiple slices with overlapping image data. For example, an image slice at a location $L_1$, includes projection data $P_{L1}$ that is 0.5 mm on either side of location $L_1$. An image slice at a location $L_2$ similarly includes projection data $P_{L2}$ that is 0.5 mm on either side of location $L_2$. Correspondingly, an image slice at a location $L_3$ includes projection data $P_{L3}$ that is 0.5 mm on either side of location $L_3$. As explained above, portions of projection data $P_{L1}$, $P_{L2}$, and $P_{L3}$ may overlap.

The projection data $P_1 \cup P_2$ acquired during the helical scan is filtered and backprojected in accordance with known reconstruction techniques to generate image data corresponding to each slice. A deconvolution algorithm is then applied to image data to generate high resolution images of the object. As described above, the redundant image data is deconvolved along the z-direction, i.e., in image space. Deconvolving the redundant image data generates deconvolved image data, which recovers the resolution within the overlapped sampled portion of the object.

The image data may be deconvolved, for example, with a three point kernel. Other kernel sizes, of course, also may be used. In the above example, the resolution approximates 0.5 mm, i.e., the CT system generates an image with 0.5 mm slice thicknesses.

The above-described embodiment utilized a 1 mm collimator aperture, and performed two helical rotations at a 0.5:1 helical pitch. However, other collimator apertures and helical pitches also may be used. Similarly, either fewer or more than two helical rotations may be performed. For example, a third helical rotation may be performed to generate even more image slices including projection data which overlaps with projection data acquired during the two previous rotations. Therefore, application of the deconvolution algorithm may provide an even smaller, i.e., better, image resolution.

While the above-described embodiments of the present invention identify deconvolving image data, the deconvolution algorithm may be applied to projection data to generate high resolution images of the object. As described above, projection data generated by overlapped z-axis sampling is substantially redundant over a portion of the object. The redundant projection data may be deconvolved along the z-direction, i.e., in projection space. Deconvolving the redundant projection data generates deconvolved projection data, which recovers the resolution within the overlapped sampled portion of the object. The deconvolved projection data may then be processed to generate deconvolved image data, from which a high resolution image is generated. X-Y resolution can be further improved by modifying the reconstruction kernel.

In addition to providing improved resolution in the z-direction, the above described embodiments facilitate improving resolution along the x-y plane. Particularly, the increased sampling and deconvolution reduce aliasing artifacts in the sampled and deconvolved data. Because of the reduced aliasing artifacts present in such data, reconstruction filter kernels with higher cut-off frequencies may be applied to such data to reconstruct an image as compared to reconstruction filter kernels currently used to filter collected data.

The above-described embodiments of the present invention provide for image generation with slices having thicknesses smaller, i.e., better, than the collimator aperture width. Particularly, the above-described embodiments generate images with a 0.5 mm slice thickness, i.e., a 0.5 mm resolution.

Such refined resolution is attained with a deconvolution algorithm which does not significantly increase the costs of a CT system. Furthermore, such improved resolution is obtained without requiring hardware and software changes in known CT systems.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including multislice systems, electron beam systems, and "fourth generation" systems wherein the detector is a full-ring stationary detector and only the x-ray source rotates with the gantry, may be used. Furthermore, while the deconvolution algorithm described herein operated in image space, the deconvolution algorithm may also be performed in projection space. In addition, while the collimator describe herein includes a 1 mm aperture, many other size collimator apertures, both larger and smaller than 1 mm, may be used. Accordingly, the spirit and scope of the invention are to be limited only by the terms of the appended claims.

We claim:

1. A method for generating image data of an object scanned by a computed tomography system, the computed tomography system including a gantry having an x-ray source which rotates around the object, said method comprising the steps of:
   obtaining projection data for at least two adjacent image slices;
   processing the obtained projection data to generate image data; and
   deconvolving the image data in a z-direction.

2. A method in accordance with claim 1 wherein obtaining projection data comprises the step of scanning the object with a helical scan.

3. A method in accordance with claim 2 wherein scanning the object comprises the step of performing a helical scan with a $0.5\beta$:$\alpha$ helical pitch, where $\alpha$ is a collimator aperture size and $\beta$ is a slice thickness.

4. A method in accordance with claim 1 wherein deconvolving the image data comprises using a kernel whose size is at least 2.

5. A method in accordance with claim 1 wherein obtaining projection data comprises the step of scanning the object with an axial scan.

6. A method in accordance with claim 5 wherein the projection data obtained for one of the image slices at least partially overlaps the projection data obtained for another of the image slices.

7. A method in accordance with claim 1 wherein deconvolving the image data comprises the step of modifying a reconstruction kernel to improve x-y resolution.

8. A system for generating image data of an object, said system comprising a gantry having an x-ray source which rotates around the object, said system configured to:
   obtain projection data for at least two image slices;
   process the obtained projection data to generate image data; and
   deconvolve the image data in a z-direction.

9. A system in accordance with claim 8 further comprising a kernel whose size is at least 2.

10. A system in accordance with claim 8 wherein to obtain projection data, said system is configured to scan the object with an axial scan.

11. A system in accordance with claim 8 wherein to obtain projection data, said system is configured to scan the object with a helical scan.

12. A system in accordance with claim 11 wherein said system is further configured to perform a helical scan with a $0.5\beta$:$\alpha$ helical pitch, where $\alpha$ is a collimator aperture size and $\beta$ is a slice thickness.

13. A method for generating data of an object scanned by a computed tomography system, the computed tomography system including a gantry having an x-ray source which rotates around the object, said method comprising the steps of:
   obtaining projection data for at least two adjacent slices;
   deconvolving the projection data in a projection space, and processing the deconvolved projection data to generate image data to produce an image having a slice thickness less than the slice thickness of the projection data adjacent slices.

14. A method in accordance with claim 13 wherein obtaining projection data comprises the step of scanning the object with a helical scan.

15. A method in accordance with claim 13 wherein scanning the object comprises the step of performing a helical scan with a $0.5\beta$:$\alpha$ helical pitch, where $\alpha$ is a collimator aperture size and $\beta$ is a slice thickness.

16. A method in accordance with claim 13 wherein deconvolving the projection data comprises using a kernel whose size is at least 2.

17. A method in accordance with claim 13 wherein obtaining projection data comprises the step of scanning the object with an axial scan.

18. A system for generating image data of an object, said system comprising a gantry having an x-ray source which rotates around the object, said system configured to:
   obtain projection data for at least two adjacent slices;
   deconvolve the projection data in a projection space; and
   process the deconvolved projection data to generate image data to produce an image having a slice thickness less than the slice thickness of the projection data adjacent slices.

19. A system in accordance with claim 18 wherein to obtain projection data, said system is configured to perform an axial scan of the object.

20. A system in accordance with claim 18 wherein to obtain projection data, said system is configured to scan the object with a helical scan.

* * * * *